United States Patent [19]

Kennard, III et al.

[11] Patent Number: 5,472,580
[45] Date of Patent: Dec. 5, 1995

[54] CATALYTIC CONVERTER DIAGNOSTIC SENSOR

[75] Inventors: Frederick L. Kennard, III, Holly; Carlos A. Valdes, Flint; Earl W. Lankheet, Grand Blanc, all of Mich.

[73] Assignee: General Motors Corporation, Detroit, Mich.

[21] Appl. No.: 257,777

[22] Filed: Jun. 9, 1994

[51] Int. Cl.⁶ ............................................. G01N 27/406
[52] U.S. Cl. ................... 204/153.1; 60/277; 204/153.18; 204/421; 204/424; 204/426
[58] Field of Search ................... 204/153.1, 153.18, 204/421–429; 60/277

[56] References Cited

U.S. PATENT DOCUMENTS

| | | |
|---|---|---|
| 3,909,385 | 9/1975 | Spielberg et al. ................... 204/427 |
| 3,941,673 | 3/1976 | Takao et al. ................... 204/427 |

OTHER PUBLICATIONS

Dr. Edelbert Hafele, "Potentiometric gas sensors" (design/function), Roth–Technik GmbH & Co., no date—9 pgs.
David M. Haaland, "Noncatalytic Electrodes for Solid–Electrolyte Oxygen Sensors", J. Electrochemical Soc., Apr. 1980, pp. 796–804.
G. Baier et al, "Non–Nernstian Zirconia Sensors for Combustion Control", Appl. Phys. A57, pp. 51–56, (1993)—Accepted 11 Mar. 1993.
A. Vogel et al., "Non–Nernstian potentiometric zirconia sensors: screening of potential working electrode materials", Sensors and Actuators B., 15–16 (1993) pp. 147–150—Aug. '93.

Primary Examiner—T. Tung
Attorney, Agent, or Firm—Cary W. Brooks

[57] ABSTRACT

Generally, the instant invention includes a method of using a sensor having an outer electrode including a gold-containing layer to diagnose the efficiency and useful life of a catalytic converter. The sensor having a gold-containing layer is positioned in an exhaust gas, combustion engine downstream from both the engine and the catalytic converter used to clean the exhaust. The sensor produces an voltage output responsive to the combustibles concentration in the exhaust gas. The voltage output from the sensor is measured and compared to a predetermined threshold correlated to a desirable combustibles concentrations in the exhaust stream or to a threshold output indicative of an inefficiently operating catalytic converter. An electrical output is then provided which is responsive to the comparison. The electrical output may be an indicator light, gauge or other devices for instructing the operator of a vehicle that the catalytic converter requires maintenance. The gold-containing layer of the sensor may be a gold alloy containing at least 28 percent by weight gold. The gold-containing layer may be the sole outer electrode of the sensor, or the gold-containing layer may be formed on a conventional platinum electrode of the sensor.

10 Claims, 6 Drawing Sheets

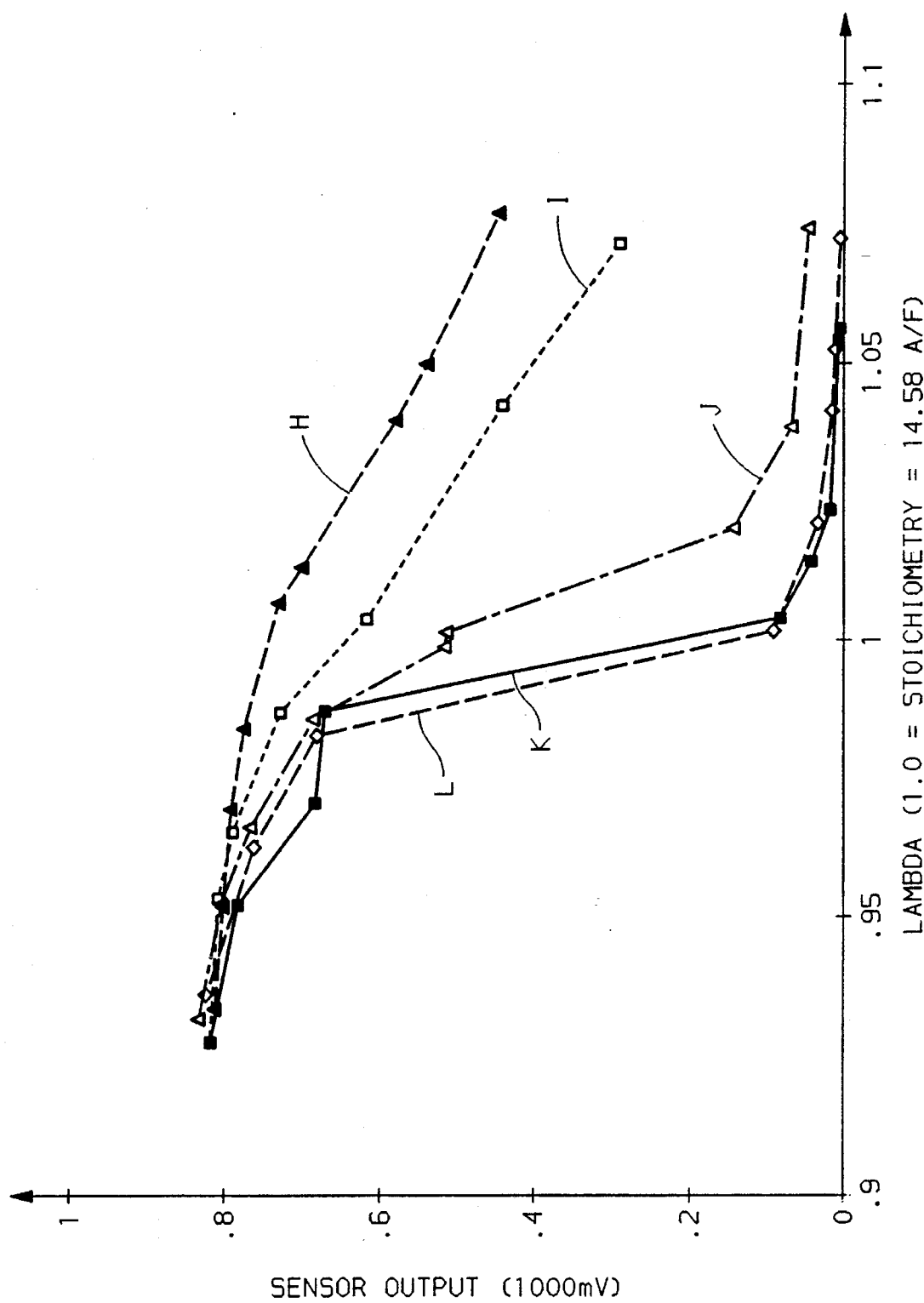

CATALYTIC CONVERTER DIAGNOSTIC SENSOR

FIELD OF THE INVENTION

This invention relates to exhaust sensors, and more particularly to an exhaust sensor having an outer or exhaust electrode including a gold-containing layer for diagnostics of catalytic converter performance.

BACKGROUND OF THE INVENTION

Conventional exhaust sensors, better known as oxygen sensors, have been utilized to monitor the exhaust from combustion engines such as those in automotive vehicles. Primarily, these oxygen sensors have been used to monitor the equilibrated oxygen content in the combustion exhaust for the purposes of controlling the fuel-to-air ratio delivered to the combustion engine so the combustion occurs at stoichiometric conditions. Such oxygen sensors utilize platinum electrodes which have a catalytic affect on the exhaust constituents passing through the electrode. Consequently, platinum electrode exhaust sensors do not accurately measure the actual constituents in the exhaust gas. They do, however, measure the equilibrium oxygen content. While systems that use a conventional oxygen sensor placed after the converter to diagnose how well the converter is performing have been developed, these suffer from the disadvantage that the sensor is not sensitive to the actual regulated constituents that define the performance of the converter.

The present invention overcomes many of the disadvantages of the prior art.

SUMMARY OF THE INVENTION

Generally, the instant invention includes a method of using a sensor having an outer electrode including a gold-containing layer to diagnose the efficiency of a catalytic converter. The sensor having a gold-containing layer is positioned in an exhaust gas of a combustion engine downstream from both the engine and the catalytic converter used to clean the exhaust. The sensor produces an electrical output responsive to the combustible concentration in the exhaust gas. The electrical output from the sensor is measured and compared to a predetermined threshold correlated to a desirable combustible concentrations in the exhaust stream or to a threshold output indicative of an inefficiently operating catalytic converter. An electrical output is then provided which is responsive to the comparison. The electrical output may be an indicator light, gauge or other devices for instructing the operator of a vehicle that the catalytic converter requires maintenance. The gold-containing layer of the sensor may be a gold alloy containing at least 28 percent by weight gold. The gold-containing layer may be the sole outer electrode of the sensor, or the gold-containing layer may be formed on a conventional platinum electrode of the sensor.

These and other objects, features and advantages of the present invention will be apparent from the following brief description of the drawings, detailed description and appended claims and drawings.

BRIEF DESCRIPTION OF THE DRAWINGS

FIG. 9 is a plot of sensor output data using converters with different efficiencies.

DETAILED DESCRIPTION

Figure 1:
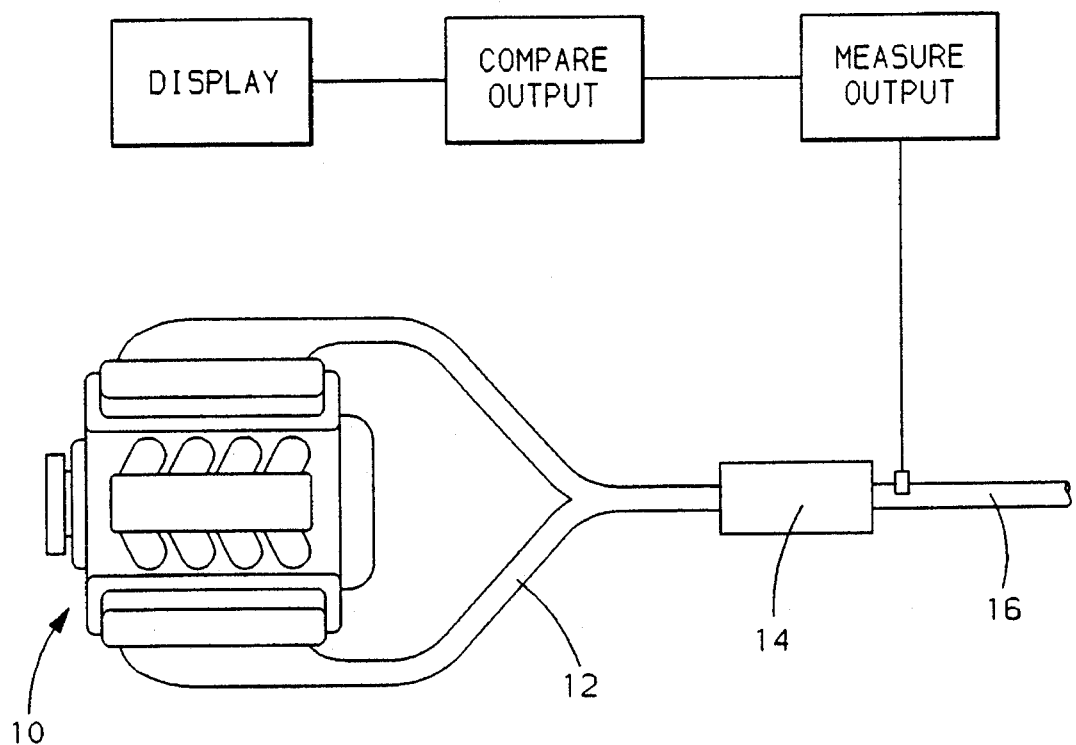
FIG. 1 illustrates a system including a combustion engine, a catalytic converter and a sensor including a gold-containing layer downstream from the catalytic converter, a means for comparing the output from the sensor to predetermined values and an output means responsive to the comparison according to the present invention.

FIG. 1 illustrates a system for diagnosing the efficiency and remaining useful life of a catalytic converter used to clean exhaust gas from a combustion engine. The system includes a combustion engine 10 including an exhaust outlet 12, a catalytic converter 14 downstream from the combustion engine, and a sensor 16 according to the present invention downstream from the catalytic converter. The system also includes a device which compares the output signal from the sensor with predetermined values responsive to a range of desirable combustibles concentration in the exhaust system. The system also includes a device for comparing the electrical output from the sensor with a predetermined threshold value associated with a high concentration of combustibles in the exhaust stream and indicative of malfunction of the catalytic converter. The device compares the magnitude of the sensor output (i.e., voltage) with predetermined levels. Upon comparing the sensor output with predetermined values, a electric signal is sent to an output device, such as an indicator light, gauge, or the like, responsive to the comparison.

Figure 2:
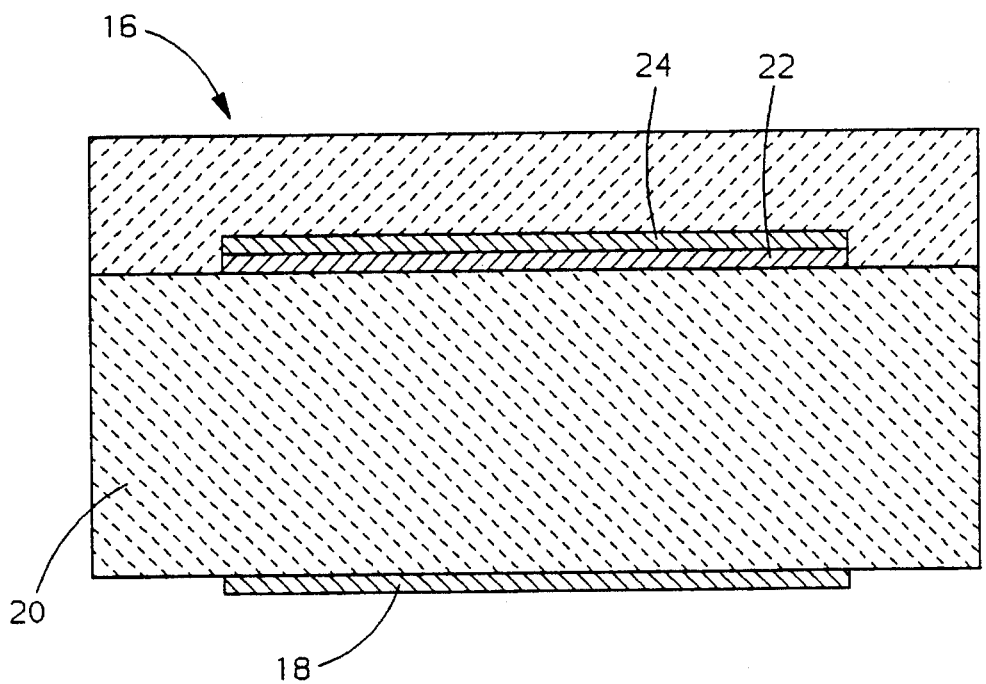
FIG. 2 illustrates a representative section of the sensing portion of a converter diagnostic sensor including a gold-containing layer according to the present invention.

FIG. 2 illustrates a sensor 16 according to the present invention which includes an inner electrode 18 which may be platinum, formed on one face of an electrolyte body 20, and an outer electrode 22 formed on an opposed surface of the electrolyte body. A suitable electrolyte body may be formed from yttria stabilized zirconia. The outer electrode 22 includes a gold-containing layer 24 according to the present invention. For example, the outer electrode may include a platinum electrode and a gold-containing layer formed on top of the platinum electrode. Alternatively, the outer electrode may be simply a single gold-containing layer. The gold-containing layer may be an alloy which contains at least 28 percent by weight gold. The gold layer may be deposited by a variety of techniques including sputtering, ink printing, or other thin and thick film deposition techniques. Preferably the thickness of the gold layer ranges from about 0.5μ to about 12μ. A protective coating such as spinel may overlie the outer electrode including the gold-containing layer.

According to the present invention, a voltage output from the sensor could be defined above which the converter would be considered to have undesirable performance characteristics. The exact specification for a particular sensor application would vary depending on the sensors temperature, electrode alloy, engine operating point and desired converter performance. In such case, an output, would be sent from the comparator to signal the operator of the vehicle that the catalytic converter needed maintenance. Such signal may activate a warning light, gauge or other display means notifying the operator.

Sensors having an outer electrode including a gold containing layer were evaluated in simulated exhaust gas mixtures to document sensor performance characteristics. Synthetic gas mixtures can be very precisely produced so that the sensor test conditions can be well controlled and accurately reproduced. Testing with synthetic gas mixtures also allows individual gas species concentrations to be varied so that the sensor sensitivity to a particular species can be determined. The composition of actual engine exhaust gas can vary due to a variety of difficult to control parameters, making precisely repeatable sensor test conditions difficult to achieve with engine testing. Sensor performance characteristics were primarily evaluated with synthetic gas mixtures and performance trends were compared to the test results obtained when actual engine exhaust was used.

The primary components present in the combustion product of a hydrocarbon fuel and air are nitrogen, carbon dioxide, water, oxygen, carbon monoxide, and hydrogen. Given basic parameters which define fuel composition and combustion conditions, the concentrations of the six primary gas components can be calculated to define a synthetic gas mixture for any air to fuel ratio. In addition the six primary components, unburned hydrocarbons and nitric oxides are also present in exhaust gas in sufficient quantities to impact sensor performance. The concentrations of these two components are not easily calculated based on combustion theory, so the concentrations used in the synthetic gas mixtures are based on empirical exhaust gas analysis data.

Figure 3:
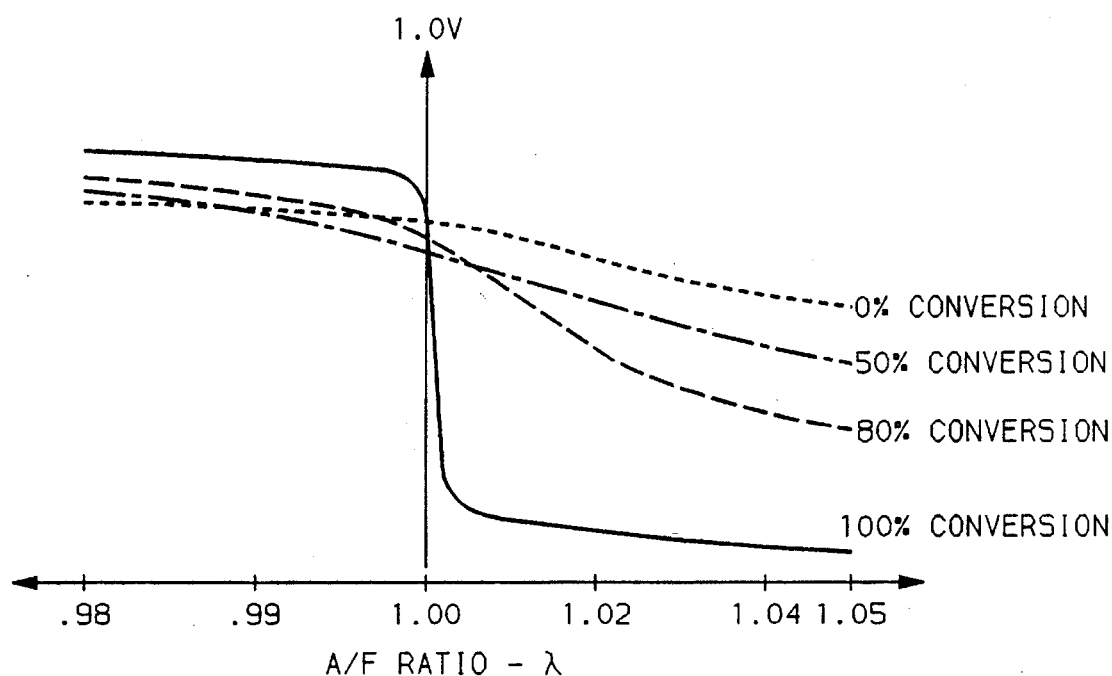
FIG. 3 is a plot of data obtained from bench gas simulation of converters with different levels of efficiency and the output of a sensor with a gold-containing electrode according to the present invention.

FIG. 3 illustrates test results of a typical sensor with a gold containing outer electrode when tested in a synthetic gas mixture as previously described. The tests were conducted over a range of normalized air/fuel ratios (LAMBDA) from a fuel rich condition of LAMBDA=0.98 to a fuel lean condition of LAMBDA=1.05 (the normalized air/fuel ratio LAMBDA is defined as the actual air/fuel ratio divided by the stoichiometric air/fuel ratio). The curve labeled "0% Conversion" resulted from using a gas mixture that simulates untreated engine exhaust. An inert catalytic converter with 0% conversion efficiency would produce this condition. The curve labeled "50% Conversion" simulates a condition where 50% of the combustible gases present in the untreated exhaust gas are oxidized. Likewise, the "80% Conversion" and "100% Conversion" curves represent conditions where 80% and 100% of the untreated exhaust combustibles are oxidized. The sensor output voltage in the fuel lean region shows a distinct relation to conversion efficiency.

Figure 4:
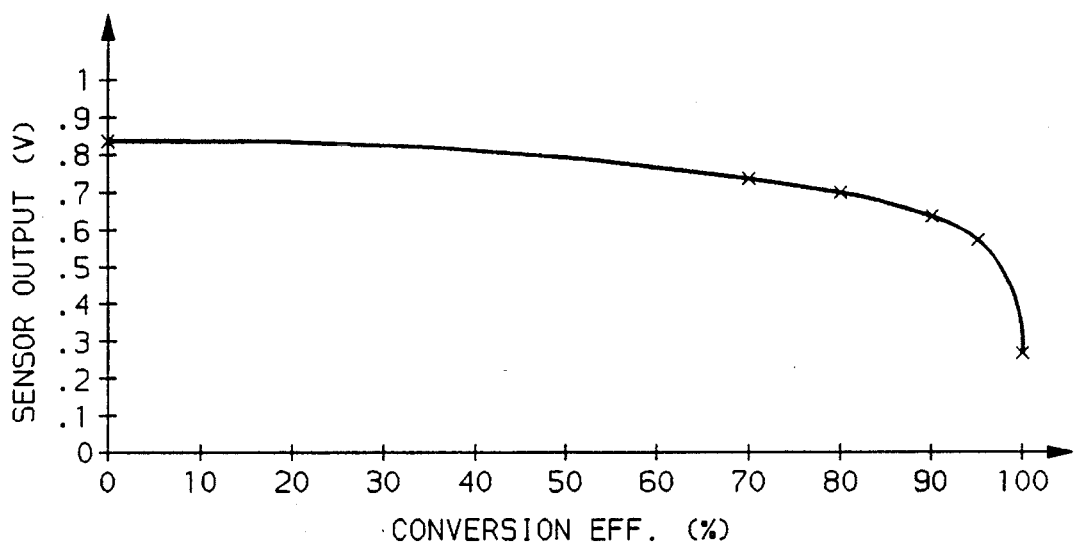
FIG. 4 is a plot of the data obtained from FIG. 3 showing the sensor output at a lean air/fuel ratio and different converter efficiencies.

FIG. 4 illustrates the voltage output of a typical sensor with a gold containing outer electrode tested in a synthetic gas mixture. In this test the normalized air/fuel ratio was fixed at a fuel lean condition of LAMBDA=1.02. The gas mixture composition was varied to simulate conditions ranging from 0% Conversion Efficiency (representing untreated engine exhaust) to 100% Conversion Efficiency (representing an ideal 100% efficient catalytic converter). This Figure illustrates that the sensor output voltage is a function of simulated catalytic converter conversion efficiency.

Figure 5:
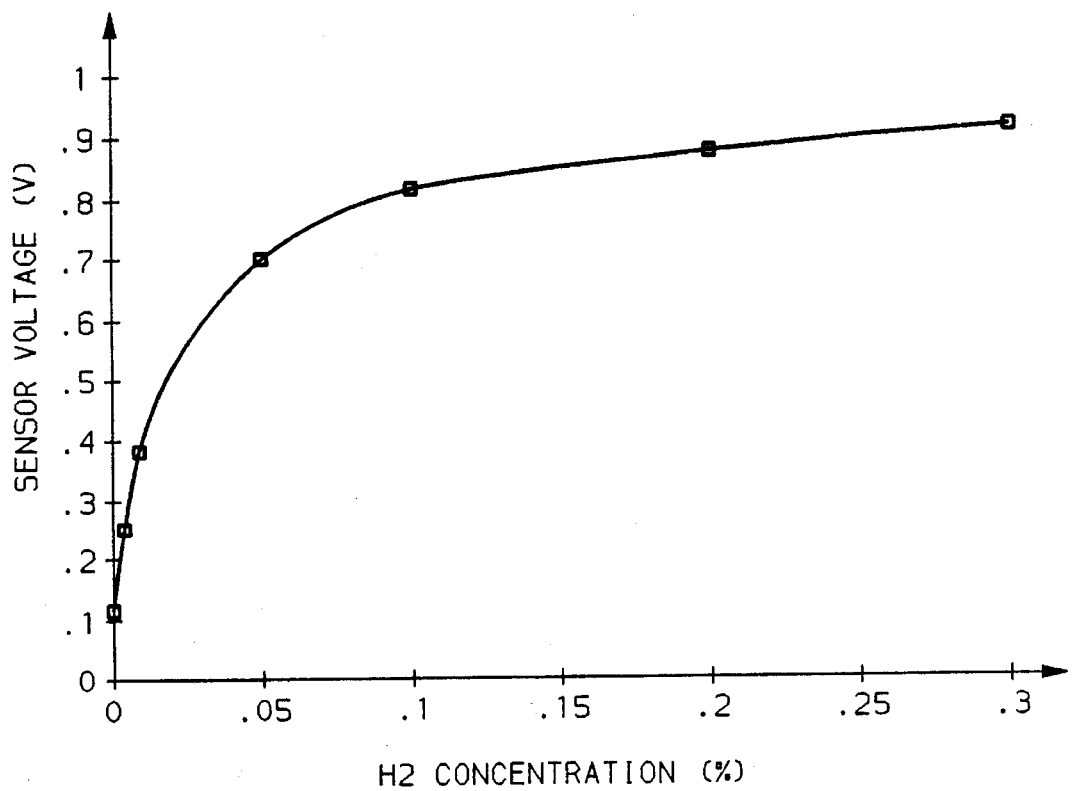
FIG. 5 is a plot of data obtained on the hydrogen sensitivity of sensor with a gold-containing exhaust electrode according to the present invention.

FIG. 5 illustrates the sensitivity of a typical sensor with a gold containing outer electrode to hydrogen concentration in the test gas. The test gas was composed of nitrogen with a fixed concentration of 0.5% oxygen. Hydrogen was added to the mixture in increasing amounts to a maximum concentration of 0.5% hydrogen. The sensor output shows a high sensitivity to low hydrogen concentrations.

Figure 6:
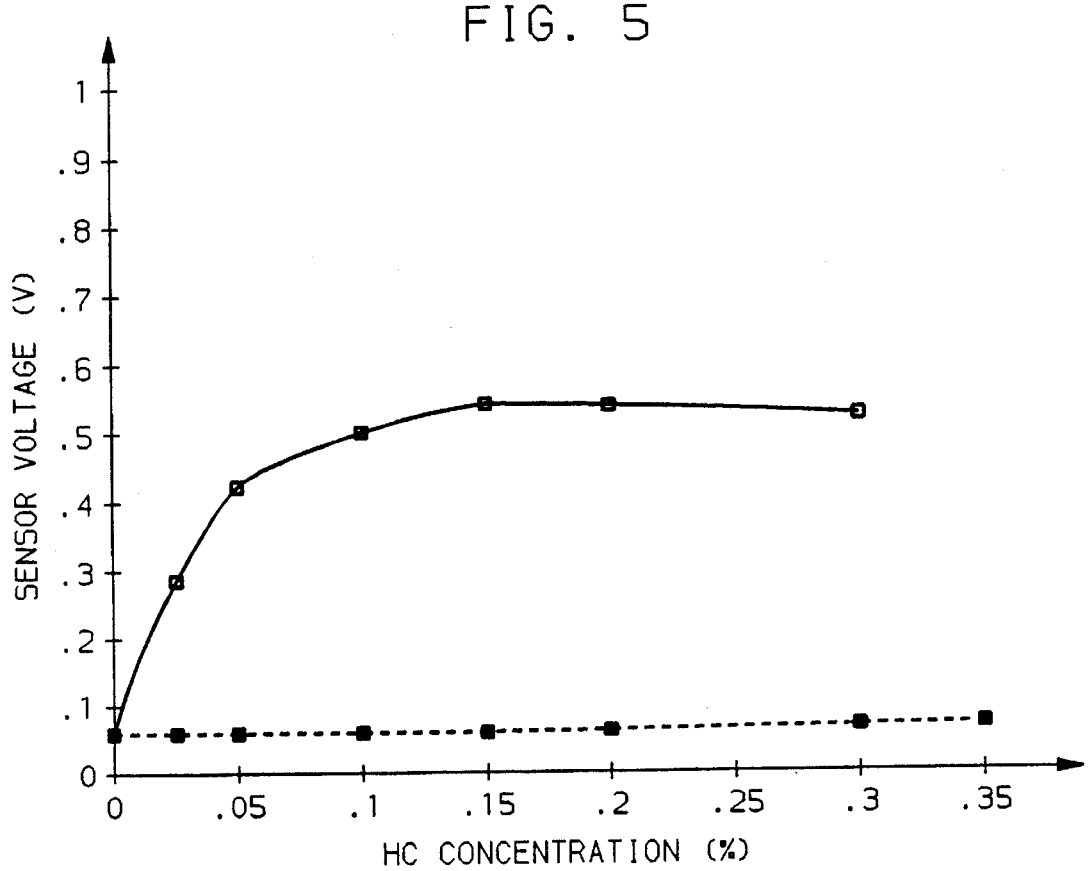
FIG. 6 is a plot of data obtained on the hydrocarbon sensitivity of a sensor with a gold-containing exhaust electrode according to the present invention.

FIG. 6 illustrates the sensitivity of a typical sensor with a gold containing outer electrode to concentrations of methane and propylene in the test gas. The test gas was composed of nitrogen with a fixed concentration of 0.5% oxygen. Methane and propylene were added individually to the mixture in increasing amounts to a maximum concentration of 0.3%. The sensor output shows a very low sensitivity to methane and a moderate sensitivity to propylene.

Figure 7:
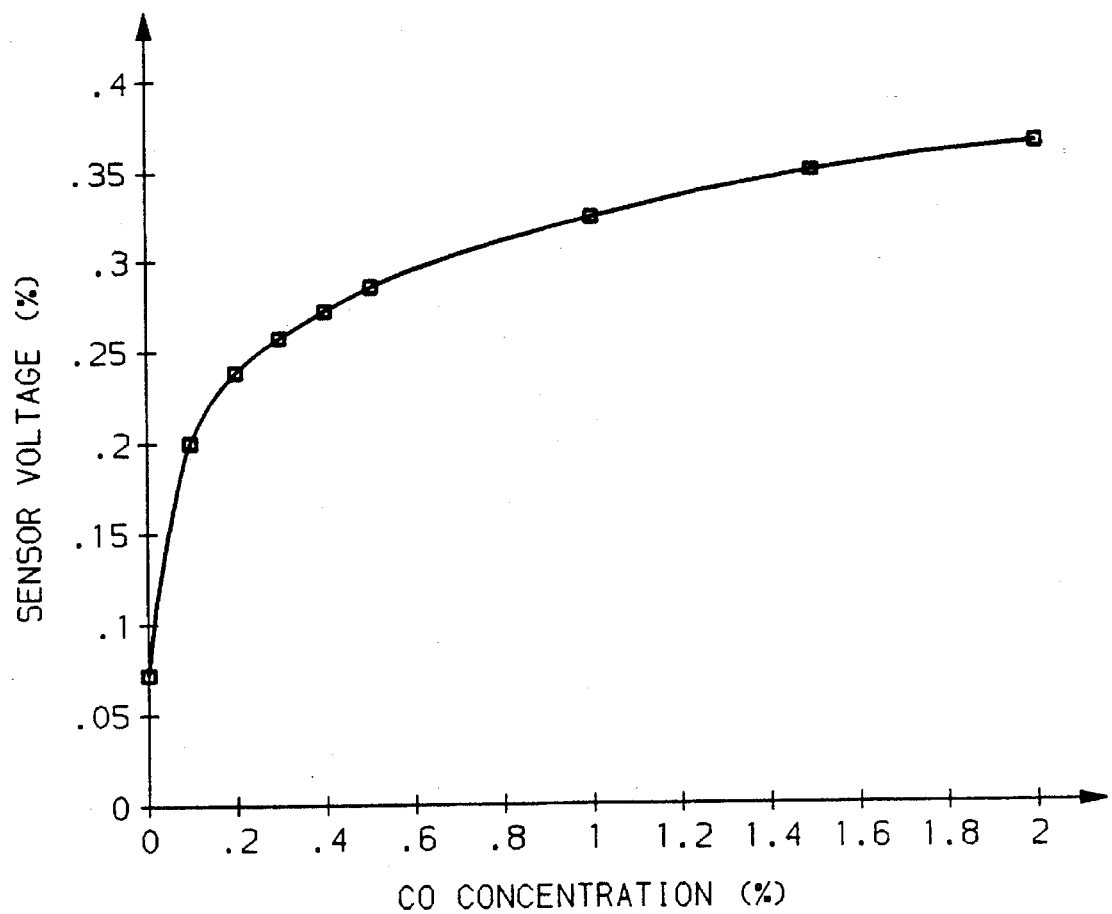
FIG. 7 is a plot of data obtained on the carbon monoxide sensitivity of a sensor with a gold-containing exhaust electrode according to the present invention.

FIG. 7 illustrates the sensitivity of a typical sensor with a gold containing outer electrode to concentrations of carbon monoxide in the test gas. The test gas was composed of nitrogen with a fixed concentration of 0.5% oxygen. Carbon monoxide was added to the mixture in increasing amounts to a maximum concentration of 4%. The sensor output shows moderate sensitivity to carbon monoxide.

Figure 8:
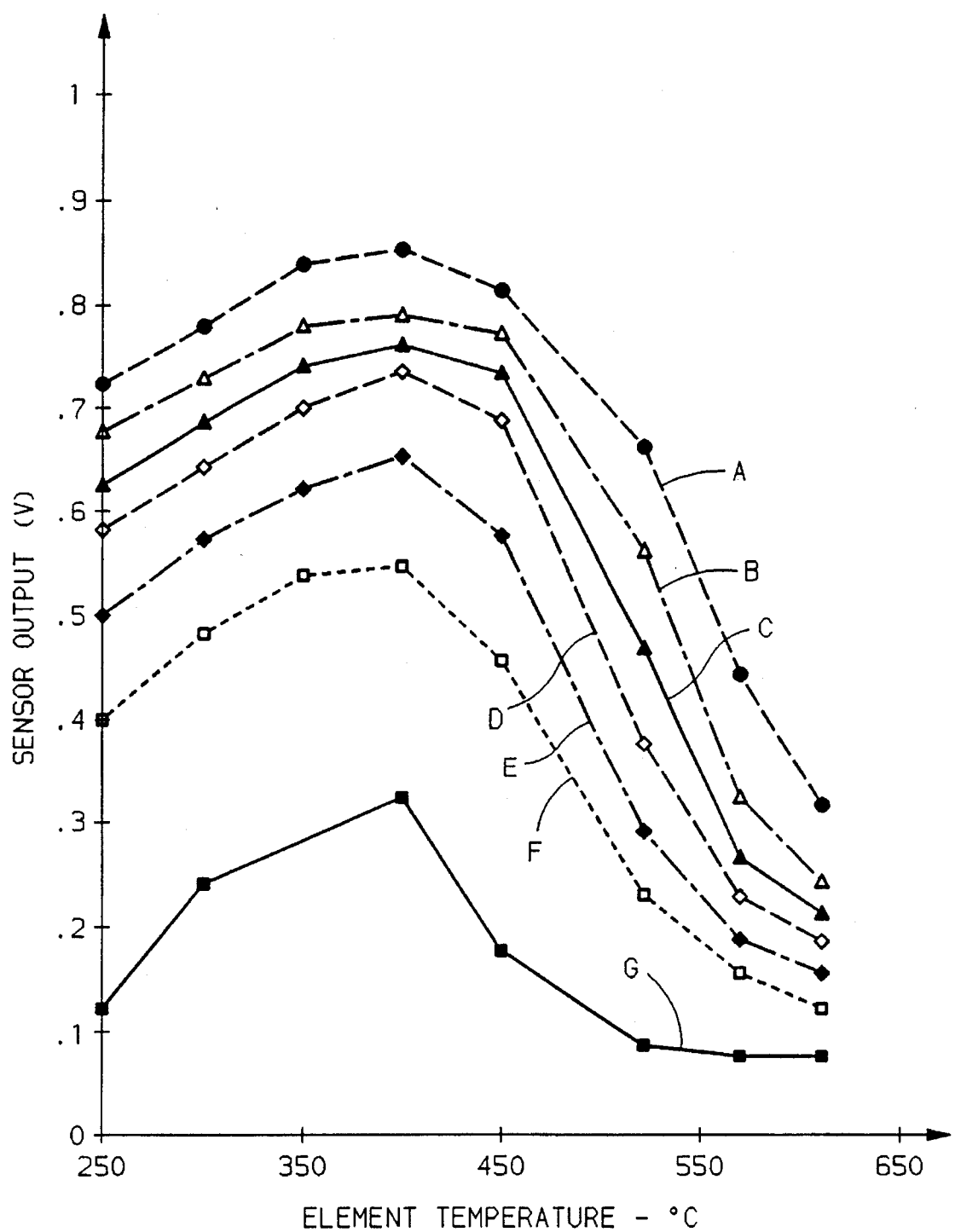
FIG. 8 is a plot of data obtained from bench gas simulation of converters with different levels of efficiency, wherein sensor voltage output is plotted as a function of element temperature at a fixed lean air/fuel ratio.

FIG. 8 illustrates the temperature sensitivity of a typical sensor with a gold containing outer electrode. The voltage output of the sensor is plotted for several simulated catalytic converter conversion efficiency levels and as a function of element temperature. The sensor output shows a sensitivity decrease at higher temperatures. Lines A, B, C, D, E, F and G correspond to data obtained using gas bench tests to simulate converter efficiencies of 0%, 50%, 70%, 80%, 90%, 95% and 100% respectively.

FIG. 9 is a plot of actual vehicle test data of the output of a sensor according to the present invention, wherein the sensor is placed after converters having different efficiencies. Lines H, I, J, K, and L correspond to data obtained for converters having 3%, 67%, 82%, 93% and 99% hydrocarbon conversion efficiency respectively.

As can be appreciated from FIGS. 3–9, a sensor according to the present invention provides the advantage of being able to diagnose the efficiency and useful life of a catalytic converter by measuring the combustibles in the exhaust leaving the converter with the sensor of the present invention.

Pure gold adhesion to ceramic oxides, such as yttrium stabilized zirconia, may not be adequate. Applying the gold onto a thin layer of Pt, Pd, Cr, Ni or Zr metals did improve adhesion to adequate levels even after annealing at high temperatures.

Gold may not be refractory enough for this application. Other refractory metals, preferably noble, can improve the temperature stability of the electrode for higher temperature applications. Alloys with a high percentage of Pt (up to 72%) operate well and increase the temperature of operation.

The invention also includes the discovery that sensor performance, accuracy, and reliability can be greatly improved by operating in specific air to fuel ratio ranges and temperature ranges. If sensor measurements are taken when the combustion engine is operating in a lean air to fuel ratio range, the efficiency of the catalytic converter can be determined much more accurately. As shown in FIG. 9, when sensor measurements are taken when LAMBDA is about 1.01 to about 1.03, the sensor output for converters having different levels of efficiency are far apart and very definable. As shown in FIG. 8, when the electrolyte body is about 350° C. to about 450° C., small deviations in temperature has the least variation on sensor output, and thus this temperature range provides for much more reliable and accurate sensor measurements and comparisons.

The embodiments of the invention in which an exclusive property or privilege is claimed is defined as follows:

1. A method of using a sensor having an outer electrode including a gold-containing layer, comprising the steps of:

positioning a sensor in an exhaust gas from a combustion engine downstream from the engine and a catalytic converter used to clean the exhaust gas, so that the sensor produces an electrical output responsive to the combustible concentration of at least one member selected from the group consisting of hydrogen, CO and hydrocarbons in the exhaust gas, said sensor comprising an outer electrode having a first layer comprising a metal and a second layer as said gold-containing layer comprising at least 28 weight percent gold, an inner electrode, and a solid electrolyte body between the electrodes;

measuring the voltage output from the sensor;

comparing the voltage output from the sensor with predetermined known voltage output values corresponding to known concentrations of said member; and providing an output responsive to the comparison, wherein the voltage output from the sensor is responsive to the concentration of said member in the exhaust gas and provides an indication of the conversion efficiency of the catalytic converter.

2. A method as set forth in claim 1 wherein the sensor output is monitored when the combustion engine is operated in a lean air to fuel ratio range.

3. A method as set forth in claim 1 wherein the output voltage from the sensor is measured when the combustion engine is operating in a lean air to fuel ratio where LAMBDA ranges from about 1.01 to 1.1.

4. A method as set forth in claim 1 wherein the output voltage from the sensor is measured when the combustion engine is operating in a lean air to fuel ratio where LAMBDA ranges from about 1.01 to about 1.03.

5. A method as set forth in claim 1 wherein the sensor output is measured when the electrolyte body has a temperature ranging from 350° C. to 450° C. to maximize sensitivity.

6. A method as set forth in claim 1 wherein said gold-containing layer further comprises another noble metal to improve stability and refractory properties of the outer electrode.

7. A method as set forth in claim 6 wherein said gold-containing layer comprises about 28 to about 99.9 weight percent gold.

8. A method as set forth in claim 1 wherein said sensor produces an electrical output responsive to the combustible concentration of hydrogen and CO.

9. A method as set forth in claim 1 wherein said sensor produces an electrical output responsive to the combustible concentration of hydrogen.

10. A method as set forth in claim 1 wherein said sensor produces an electrical output responsive to the combustible concentration of CO.

\* \* \* \* \*